(12) United States Patent
Hall

(10) Patent No.: US 10,912,288 B1
(45) Date of Patent: Feb. 9, 2021

(54) HABITAT AND SYSTEM FOR CULTIVATION OF INSECTS

(71) Applicant: ASPIRE FOOD GROUP LTD, Toronto (CA)

(72) Inventor: Michael Todd Hall, Austin, TX (US)

(73) Assignee: ASPIRE FOOD GROUP LTD, Toronto (CA)

(*) Notice: Subject to any disclaimer, the term of this patent is extended or adjusted under 35 U.S.C. 154(b) by 182 days.

(21) Appl. No.: 15/725,420

(22) Filed: Oct. 5, 2017

Related U.S. Application Data

(60) Provisional application No. 62/405,026, filed on Oct. 6, 2016.

(51) Int. Cl.
*A01K 67/033* (2006.01)
*A23K 50/90* (2016.01)
*A01K 29/00* (2006.01)

(52) U.S. Cl.
CPC ............ *A01K 67/033* (2013.01); *A01K 29/00* (2013.01); *A23K 50/90* (2016.05)

(58) Field of Classification Search
CPC .. A01K 67/033; A01K 67/0339; A01K 29/00; A23K 50/90
USPC ..... 119/6.5, 6.6, 65, 78, 408, 454, 456, 464, 119/475, 515, 521, 51.5, 72
See application file for complete search history.

(56) References Cited

U.S. PATENT DOCUMENTS

| | | | | |
|---|---|---|---|---|
| 1,624,245 A * | 4/1927 | Holmes | ................ | A01K 39/01 222/611.1 |
| 1,885,854 A * | 11/1932 | Montellano | ............ | A01M 1/08 43/139 |
| 2,569,722 A * | 10/1951 | Knox | ...................... | A01M 1/06 43/139 |
| 3,295,500 A * | 1/1967 | Blough | ................ | A01K 5/0283 119/51.5 |
| 7,661,391 B2* | 2/2010 | Sia | ......................... | A01K 31/14 119/302 |
| 7,729,806 B2* | 6/2010 | Ohira | ....................... | B66B 1/34 187/247 |
| 7,805,882 B2* | 10/2010 | Wolf | ..................... | A01M 3/005 43/133 |
| 8,001,650 B2* | 8/2011 | Trotter | ..................... | A47L 5/38 15/314 |
| 9,335,413 B2* | 5/2016 | Weber-Grabau | ....... | G01N 21/00 |
| 9,510,572 B2* | 12/2016 | Aldana | ................ | A01K 67/033 |
| 2008/0178819 A1* | 7/2008 | Sia | ........................ | A01K 31/00 119/300 |
| 2010/0186284 A1* | 7/2010 | Hyde | .................... | A01M 1/226 43/132.1 |
| 2017/0142945 A1* | 5/2017 | Demetrescu | ....... | G01N 35/0099 |
| 2020/0253176 A1* | 8/2020 | Fotiadis | ................ | A23K 50/75 |

* cited by examiner

*Primary Examiner* — Ebony E Evans
(74) *Attorney, Agent, or Firm* — Lee & Hayes, P.C.

(57) ABSTRACT

A harvesting platform configured to navigate in a space over a room configured for the cultivation of insects. The harvesting platform may be equipped with a watering device and feed delivery device for supplying nutrients to the insect population being cultivated within the room. The harvesting platform may also be equipped with a harvesting device, such as a vacuum system, to harvest or remove the insects from the room when matured.

20 Claims, 14 Drawing Sheets

HABITAT AND SYSTEM FOR CULTIVATION OF INSECTS

CROSS-REFERENCE TO RELATED APPLICATION(S)

This application claims priority to U.S. Provisional Application No. 62/405,026 filed on Oct. 6, 2016 and entitled "HABITAT AND SYSTEM FOR CULTIVATION OF INSECTS," which is incorporated herein by reference in its entirety.

BACKGROUND

Today most insects that are cultivated for human consumption are housed in single use cardboard boxes or immobile large troughs made of wood or concrete. Cardboard boxes are disposed after each use and add significant expense to the cultivating and harvesting process. Additionally, the cardboard boxes are typically moved around by hand and the insects are watered and fed by hand. This leaves the insects susceptible to damage or loss during the period of time when a human must interact with them. For example, the small larva may be removed from the cardboard box with the feeding or watering apparatus during a feeding or watering cycle if the human is not careful. The large troughs made of wood or concrete, are susceptible to pathogenic and fungal activity which may devastate insect populations and materially impede production. This results in substantial economic loss and wastage.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
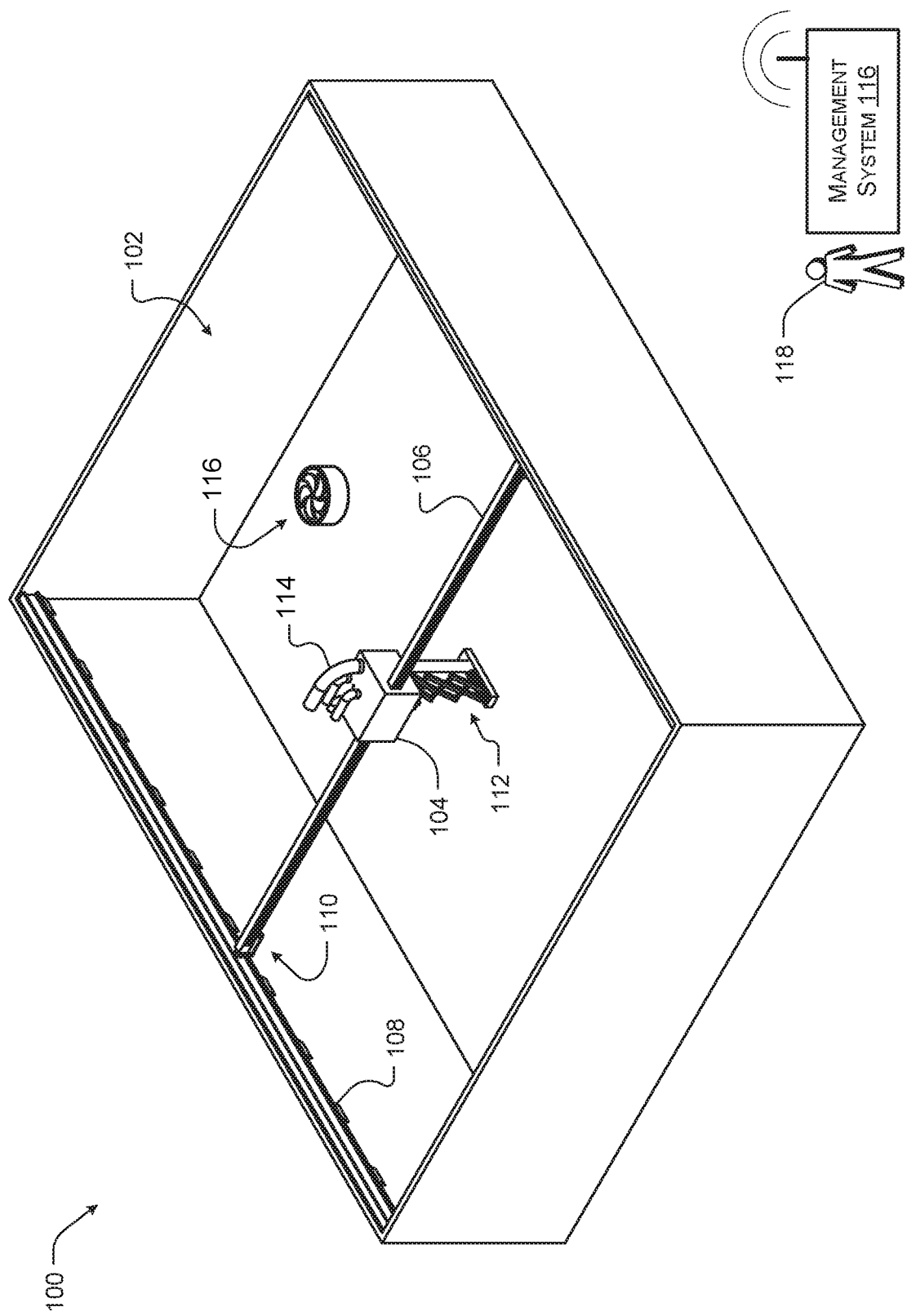
FIG. 1 illustrates an example system for cultivating insects according to some implementations.

Described herein are implementations and techniques for providing an automated habitat and cultivating system for raising insects. For example, the system may include a room configured to hold or house multiple insect habitats. The room may be configured with a feed and water delivery platform and/or a harvesting platform mounted to the walls or ceiling above the insects and habitats. In some cases, described herein the feed, water, and harvesting platforms may be integrated into a single platform, referred to herein as the harvesting platform. In one example, the room may be configured with a medium that eggs of insects, such as crickets, grasshoppers, mealworms, and/or other insects that have a flightless stage, may be suspended. The insects may then hatch into the room where the insects may live substantially free of human or outside contact reducing risk of exposure to invasive pathogens.

In some examples, the room may include habitats that are placed at various locations (e.g., rows or other patterns) along the room floor. The habitats may be included to increase the overall total surface area within the same volume previously contained within the room by as much as 25×. For instance, the larger the surface area within the room, the more insects that may be contained or cultivated within, thereby improving overall yields per-volume. For example, every two square inches of increased surface area within a room has the potential to increase a cricket population within the room by one. In some examples, other designs of habitats may increase the total surface area by other multipliers such as 20×, 30×, or 40×.

The habitats contained within the room may generally form a grid, helix or cross-section within the interior space of the room. The habitats may be formed from various materials that allow the insects to climb and/or migrate over the vertical walls of the insert. For example, the surface of the habitats may be rough or have a high coefficient of friction (e.g., greater than 0.5). Thus, the habitats are able to increase the surface area available to the insects within the room. In some cases, the habitats are designed to be removable from the room or lifted off the floor of the room after harvesting of the insects to allow for cleaning of the room, replacement of hatching medium, laying of eggs, etc. For instance, the room may be equipped with ceiling or wall mounted apparatus that may secure to the habitats to lift them, while the waste reaming on the floor is removed and the room is prepared for hatching another crop of insects. In one particular case, the harvesting platform may be equipped to lift the habitats as well as perform the waste removal. For instance, this may include an arm that locks with the habitat and lifts the habitat while a vacuum or other waste removal device removes the contents on the floor of the room following harvesting.

In some cases, the harvesting platform or platforms may be mounted above the habitats such that the harvesting platform may navigate around the room to distribute feed, deliver water to, for instance, water trays on the habitats, and to harvest the insects via a vacuum based system. For example, two parallel beams may be mounted along two opposing walls of the room to suspend a third beam. The harvesting platform may be mounted to the third beam, such that the harvesting platform may move in a first direction and second direction opposite the second direction along the two parallel beams and the harvesting platform may move in a third direction perpendicular to the first direction and the section direction and a fourth direction opposite the third direction along the third beam. In other example, the harvesting platform may be suspended via cables that may be retracted and extended to allow the harvesting platform to move over the habitats within the room.

The harvesting platform may be configured to traverse a predetermined pattern over the room when distributing feed. For example, the feed may be distributed over the floor in a random or substantially even pattern. In this example, since the insects are not contained within an enclosure and the room is free of human exposures, the feed may be distributed along the floor where the insects may locate and consume. Thus, removing any requirement that the feed be delivered onto feed trays or to a specific location.

However, when delivering water, the harvesting platform may be configured to identify or locate water trays positioned throughout the room. For example, the water trays may be positioned on top of the habitats to encourage the insects to climb or spread out along the vertical space provided to further increase population density within the room. The harvesting platform may be equipped with sensors and/or image components that may collect data that is usable to determine a position of the harvesting platform within the room, identify the water tray, and assist the harvesting platform with aligning with the water tray in order to deposit water onto the tray.

In some cases, the harvesting platform may also include a harvesting device, such as a vacuum system. During harvesting, the harvesting platform may align the harvesting device with the tops of the habitats and move along the habitat removing the insects. In some cases, a level of suction applied by the harvesting device may be configured to remove insects within the top 25%, 50%, 80%, or 95% of the habitat. In this manner, the harvesting platform may collect only live insects as the dead insects and waste material is located on the floor of the room. In some instances, the harvesting platform may make several harvesting passes along each habitat to collect the entire population. As on the first pass, some of the insects may be below the level at which the suction is able to remove them. However, as the insects are removed from the room, the insects on the floor typically seek shelter of the habitats climbing up the vertical walls into the range of the harvesting device. Thus, on the subsequent passes the remaining population may be harvested.

FIG. 1 illustrates an example system 100 for cultivating insects according to some implementations. In the current example, the system 100 includes a room 102 for housing insects in an environment. A harvesting platform 104 is positioned above the floor of the room 102. In the current example, the harvesting platform 104 is positioned on a first beam 106 to allow movement in a first and second direction (e.g., to the left and right) within the room. For instance, the harvesting platform 104 may slide along the beam 106 to position itself within the room 102. The beam 106 is further coupled to two parallel wall mounted beams, generally indicated by 108. The beam 106 is coupled to each of the parallel wall mounted beams 108 via a mounting device 110. In the current example, the mounting device 110 on the left and right hand side of the room allows the beam 106 to move along the parallel wall mounted beams 108 in a third and fourth direction (e.g., forward and backwards direction) within the room 102. In this manner, the harvesting platform 104 may be positioned over any location within the room 102.

The harvesting platform 104 is equipped with a harvesting device 112. In the current example, the harvesting device 112 is a retractable vacuum system that allows the harvesting platform 104 to extend downward into the room 102 and to remove insects located on various habitats or structures within the room 102. For example, the habitats may be included within the room 102 to increase the overall total surface area within the same volume previously contained within the room 102 by, as the larger the surface area within the room 102, the more insects that may be contained or cultivated within, thereby improving overall yields per-volume. In some cases, the habitats may be a grid or cross sections that extend upward into the room by three feet, five feet, seven feet, or in some instances as high as twelve feet from the floor of the room 102.

Harvesting platform 104 may be configured to position over or align with the habitats, lower the harvesting device 112 to within a predefined distance of the top surface of the habitat (e.g., less than two inches, less than one inch, less than 6 centimeters, etc.), apply a suction or vacuum which causes the insects on the walls of the habitat to be drawn into a collection tube, such as collection tube 114, and ultimately deposited in a collection area or bin outside the room 102.

In some cases, the suction of the harvesting device 112 may be configured to apply a level of suction to remove insects within the top 25%, 50%, 80%, or 95% of the habitat. In this manner, the harvesting platform 104 may collect only live insects as the dead insects and waste material is located on the floor of the room 102. In some instances, the harvesting platform 104 may make several harvesting passes along each habitat to collect the entire population. As on the first pass, some of the insects may be below the level at which the suction is able to remove them. However, as the insects are removed from the room, the insects on the floor typically seek shelter of the habitats climbing up the vertical walls into the range of the harvesting device 112. Thus, over time the remaining population may be harvested.

In the illustrated example, the system 100 and the harvesting platform 104 are shown within one room 102 of insects. However, in some cases, the system 100 and/or the harvesting platform 104 may be configured to harvest insects and/or provide feed and water to multiple rooms of insects. For instance, rooms may be situated adjacent to each other and the beams 108 may extend over multiple rooms to allow the harvesting platform 104 to move through an opening at the top of the wall between the two adjacent rooms.

In one example, the room 102 may be equipped with an agitation device 116 to cause the insects to migrate off of the floor of the room 102 and onto a habitat, such hat the insects may be harvested by the harvesting platform 104 without the harvesting platform 104 collecting any waste located on the floor of the room 102. In the current example, the agitation device 116 may be fan or other vibrational means. In other cases, the agitation device 116 may cause a local temperature change (e.g., generate heat), may introduce noise or other audio stimulus, etc. In some cases, the agitation device 116 may be incorporated into the floor and/or wall of the room 102, such that the entire floor area may be configured to vibrate, heat, cool, etc.

In the illustrated example, a management system 116 may be configured to coordinate the movement of the harvesting platform 104 as well as the feed and water delivery and the harvesting process. For example, the management system 116 may provide instructions to the harvesting platform 104 based on data received from individual habitats, the harvesting platform 104 itself or other sensors associated with the room 102. The management system 116 may also be configured to process the sensor and image data collected by the harvesting platform 104 to reduce the overall cost of each of the harvesting platform 104. For instance, the management system 116 may receive image data associated with the room 102 and determine the amount of feed to be dispensed by the harvesting platform 104.

In other examples, the management system 116 may be configured to provide notifications or alerts to an operator or administrator 118 of the system 100 in response to identifying various issues associated with the operation of the room 102 or harvesting platform 104. For instance, the management system 116 may issue an alert if the sensor or image data indicates that an obstruction is blocking the progress of the harvesting platform 104 or an operation associated with the harvesting platform 104. In some cases, the management system 116 may also alert the operator 118 in the event that the sensor and/or image data collected by the room 102 or the harvesting platform 104 indicates that the insect population is unhealthy, dying, or suffering from any unexpected issue (such as a pathogen).

In one specific example, the management system 116 may allow the operator 118 to manually control the harvesting platform 104. For example, the operator 116 may control the harvesting platform 104 via a user interface associated with the management system 116. In this manner, the operator 118 may control the placement of water and feed within the room 102. The operator 118 may also control the harvesting of the insect population to ensure quality standards.

In some specific examples, the harvesting platform 104 may be configured to traverse the same path at one or more times per day (e.g., at feeding time or watering time). In this example, the harvesting platform 104 may determine that a period of time has elapsed since the last feeding or watering.

Figure 2:
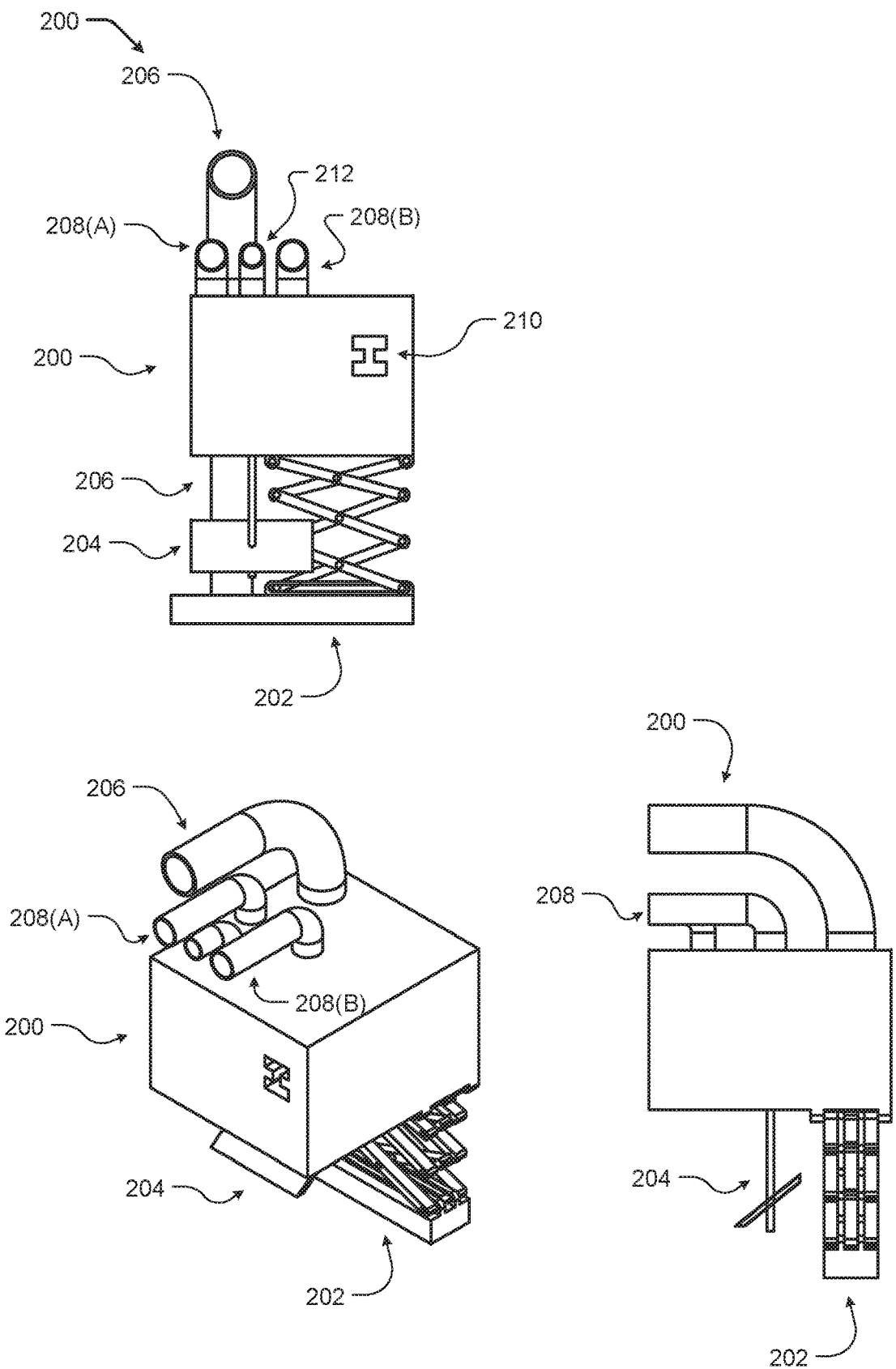
FIG. 2 illustrates an example harvesting platform for use in the system of FIG. 1 according to some implementations.

FIG. 2 illustrates an example harvesting platform 200 for use in the system 100 of FIG. 1 according to some implementations. In the current example, the harvesting platform 200 is equipped with a harvesting device 202 and a feed distribution device 204. In the current example, the harvesting device 202 is a retractable vacuum system that allows the harvesting platform 200 to extend downward into a room and to remove insects located on various habitats or structures within the room. For example, the harvesting platform 200 may be configured to position over or align with the habitats, lower the harvesting device 202 to within a predefined distance of the top surface of the habitat (e.g., less than two inches, less than one inch, less than 6 centimeters, etc.), apply a suction or vacuum which causes the insects on the walls of the habitat to be drawn into a collection tube, such as collection tubes 206, and ultimately deposited in a collection area or bin outside the room. In the present example, the harvesting device 202 is coupled to the flexible collection tube 206 which may extend downward with the harvesting device 202 and move with the harvesting platform 200 as the platform 200 navigates throughout the room.

In some cases, the suction of the harvesting device 202 may be configured to apply a level of suction to remove insects within the top 25%, 50%, 80%, or 95% of the habitat. In this manner, the harvesting platform 200 may collect only live insects as the dead insects and waste material is located on the floor of the room. In some instances, the harvesting platform 200 may make several harvesting passes along each habitat to collect the entire population. As on the first pass, some of the insects may be below the level at which the suction is able to remove them. However, as the insects are removed from the room, the insects on the floor typically seek shelter of the habitats climbing up the vertical walls into the range of the harvesting device 202. Thus, over time the remaining population may be harvested.

In the current example, the feed distribution device 204 is shown as a flat angled member. In some cases, feed is dropped onto the angled member of the feed distribution device 204 from a feed tube 208. As the feed hits the flat angled member, the feed is distributed into the room. In the current example, the feed is intended to be distributed evenly or substantially even along the floor of the room. For example, the feed may be dropped from the feed tube 208 onto the angled member as the harvesting platform 200 moves throughout the room. In some instances, the angled member may be equipped with pips, grooves, bumps, davits, or other type of deflecting apparatus, to cause feed to more evenly or widely distribute.

In the current example, the harvesting platform 200 is shown with two feed tubes 208(A) and 208(B) for dispensing feed onto the feed distribution device 204. For instance, at various stages or on various schedules the insects within the room may require different nutritional feed mixes or types. Thus, by including multiple feed tubes 208(A) and 208(B), the harvesting platform 200 may distribute the different nutritional mixes or types of feed without requiring an operator to empty and refill a feed hopper. In some cases, the harvesting platform 200 may include more than two feed tubes. For example, if the harvesting platform is configured to supply feed to multiple rooms that each may house different types of insects or insects at different life cycle stages; where the makeup of the feed may vary from room to room.

The harvesting platform 200 is also shown with an opening 210 for receiving a beam that the harvesting platform 200 may use to navigate back and forth along in a first and second direction. The harvesting platform 200 also includes a water tube 212 for distributing water to the insects within the room, as will be described in more detail below.

Figure 3:
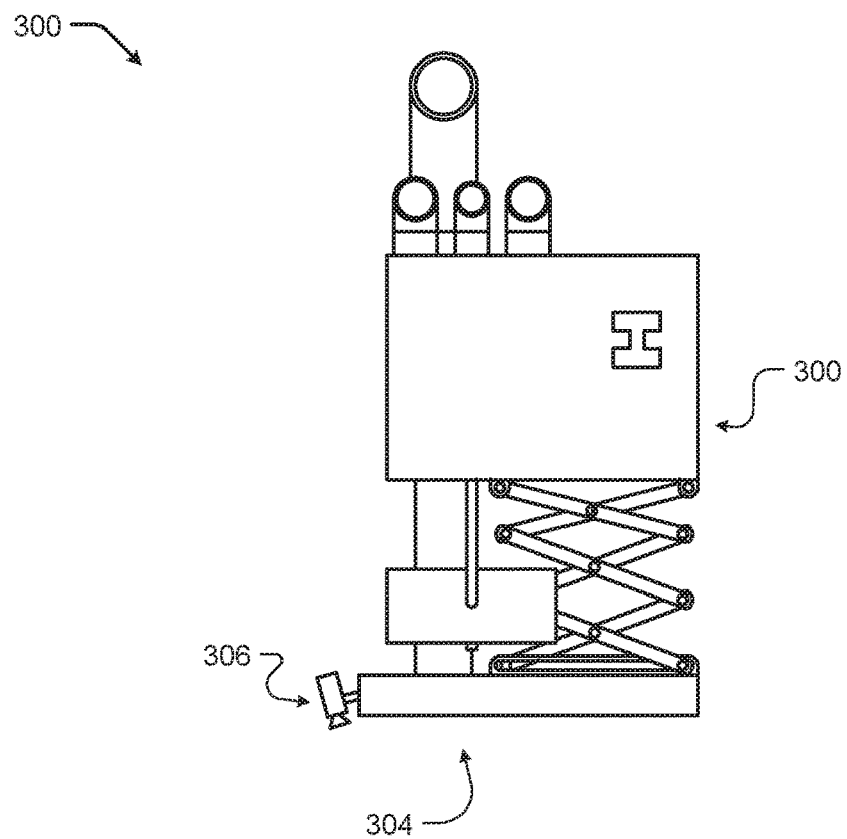
FIG. 3 illustrates another example harvesting platform position relative to a habitat within the system of FIG. 1 according to some implementations.
Figure 3:
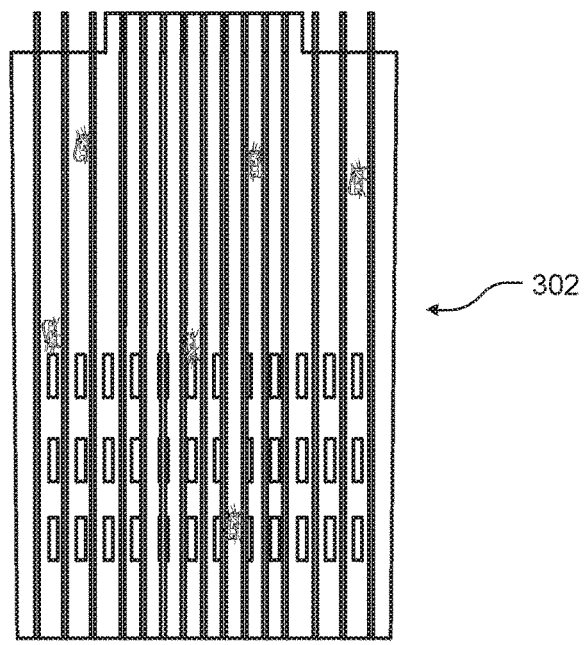

FIG. 3 illustrates another example harvesting platform 300 position relative to a habitat 302 within the system 100 of FIG. 1 according to some implementations. In the current example, the harvesting platform 300 is the process of positioning the harvesting device 304 to collect the insects from the habitat 302. The harvesting platform 300 may first align with the habitat 302 by analyzing data collected by various sensors and image components 306. For example, the harvesting platform 300 may be equipped with one or more global satellite position (GPS) sensors, inertial measurement units (IMU), gyroscopes, accelerometers, cameras (e.g., depth cameras, red-green-blue cameras, etc.), heat sensors, temperature sensors, etc. In one specific example, the image components may include a projector or light emitting component that may be used as part of a spacial recognition system.

Figure 4:
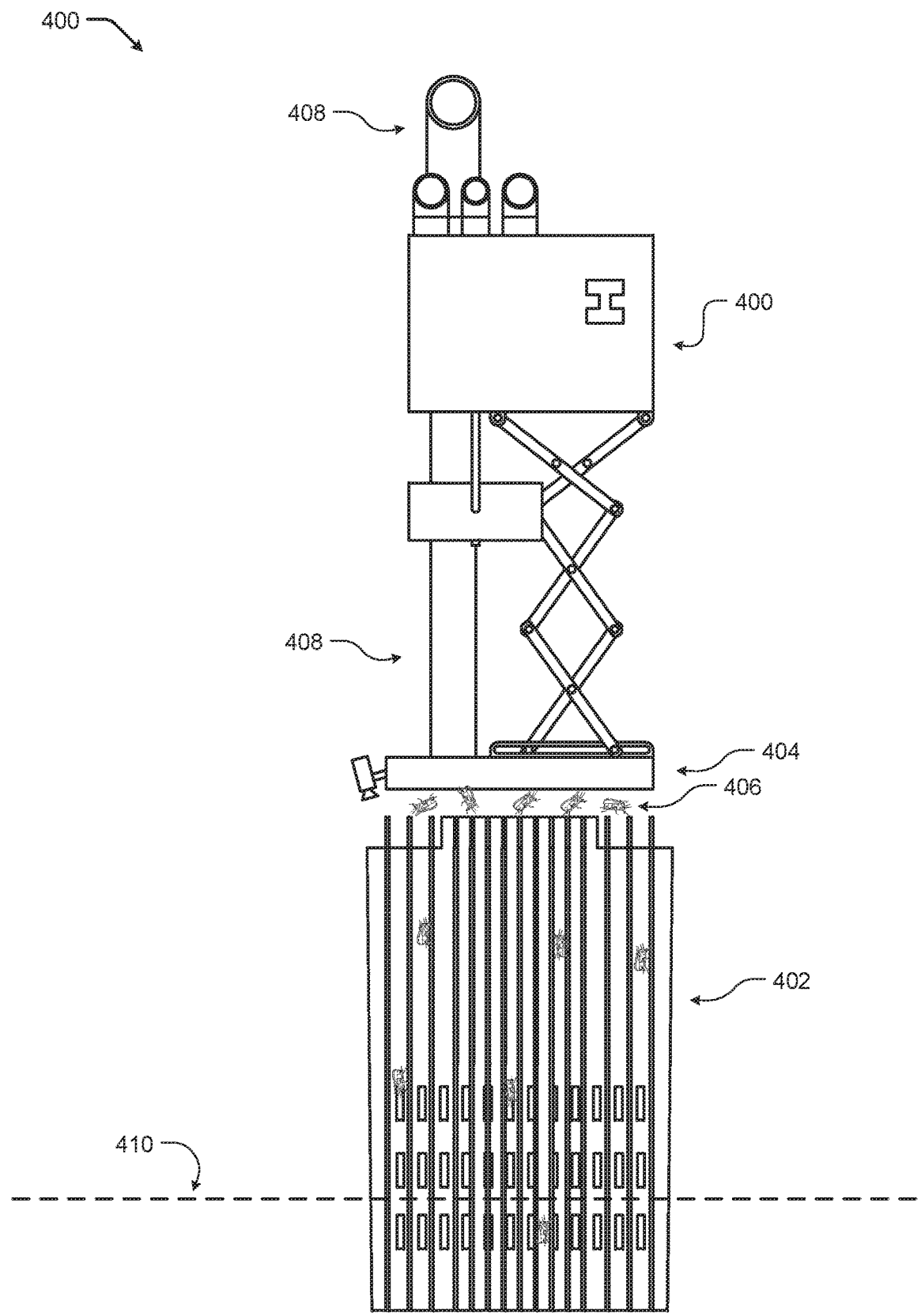
FIG. 4 illustrates another example harvesting platform position relative to a habitat within the system of FIG. 1 according to some implementations.

FIG. 4 illustrates another example harvesting platform 400 position relative to a habitat 402 within the system 100 of FIG. 1 according to some implementations. In the current example, the harvesting platform 400 has aligned with the habitat 402 and extended the harvesting device 404 downward to a positioned above the top surface of the habitat 402. The harvesting platform 400 has activated the harvesting device 404 and insects 406 are being removed or vacuumed out of the habitat 402, as shown.

As the insects 406 are captured by the harvesting device 404, the insects 406 are sent to a collection bin or area via flexible tubing 408. The suction applied by the harvesting device 404 may be configured to remove insects above a threshold level off the floor or a threshold distance from the harvesting device 404, generally indicated by the line 410. For instance, the threshold level may be six inches, one-foot, two feet, or other distances from the floor of the room. In this manner, only live insects may be harvested from the room improving the overall quality of the crops.

In some examples, the suction from the harvesting device 404 may also be used as a kill system, such that the suction levels may be set about a threshold that causes a deadly trauma to the insects. In this manner, the harvesting device 404 may be used to harvest and to euthanize the insect populations as a single system.

Figure 5:
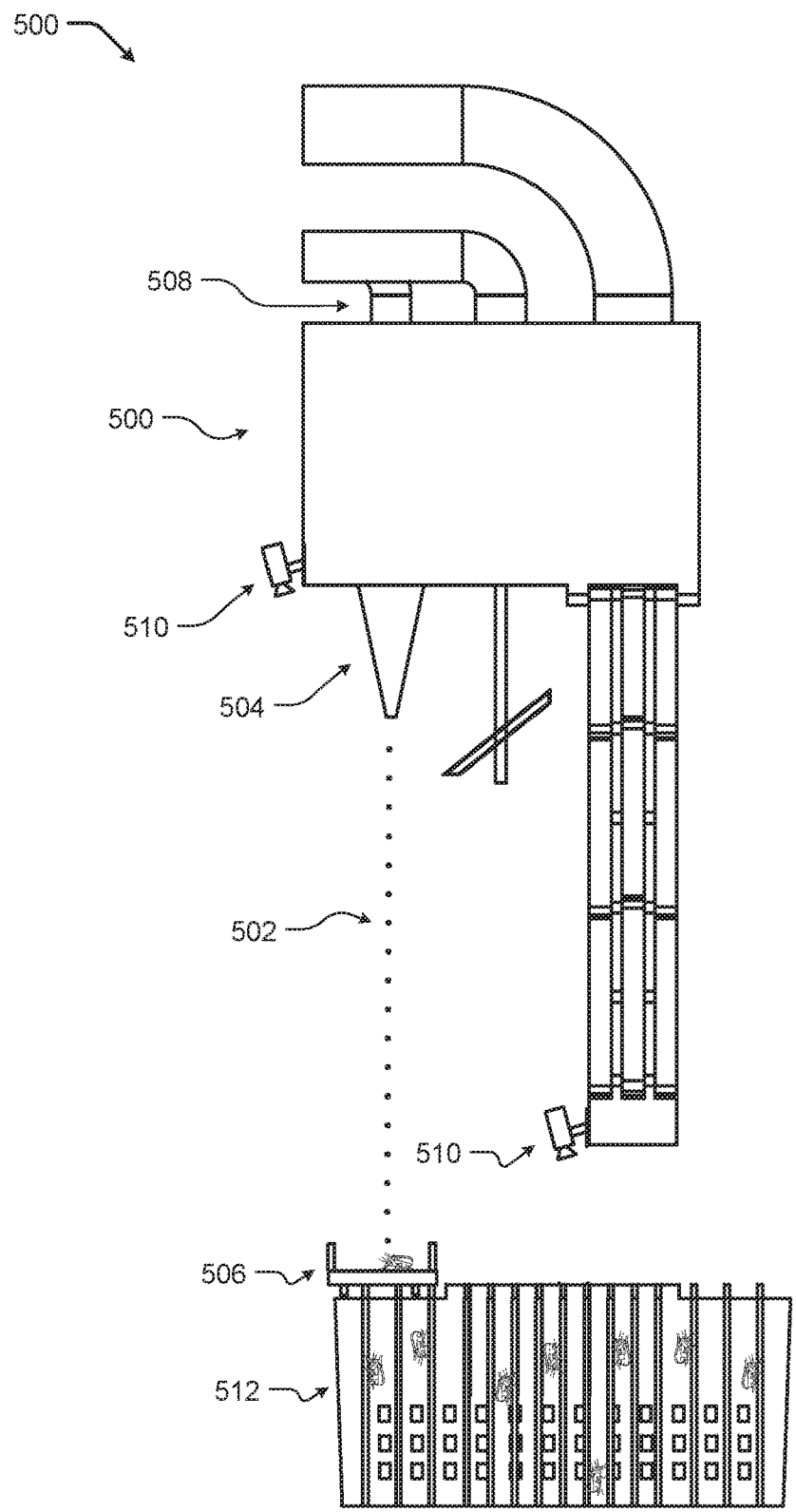
FIG. 5 illustrates another example harvesting platform position for water delivery according to some implementations.

FIG. 5 illustrates another example harvesting platform 500 position for water 502 delivery according to some implementations. In the current example, the harvesting platform 500 is equipped with a water dispenser 504 to provide water to a water tray 506 within the room. For instance, the harvesting platform 500 may be coupled to a water source (not shown) via a water tube 508. In some cases, the harvesting platform 500 may dispense water while dispensing feed and/or harvesting insects from the room.

In the present example, the harvesting platform 500 is the process of delivering the water 502 onto the water tray 506 for supplying water to the insects within the room. The harvesting platform 500 may first align with the habitat 512 by analyzing data collected by various sensors and image components 510. Unlike the feed distribution, discussed below with respect to FIG. 6, the water 502 cannot be spread over the floor of the room but rather dispensed into the water trays 506. Thus, in some cases, the harvesting platform 500 may be configured to position the water dispenser 504 with the tray 504 in lieu of or in addition to aligning with the habitat 512.

Figure 6:
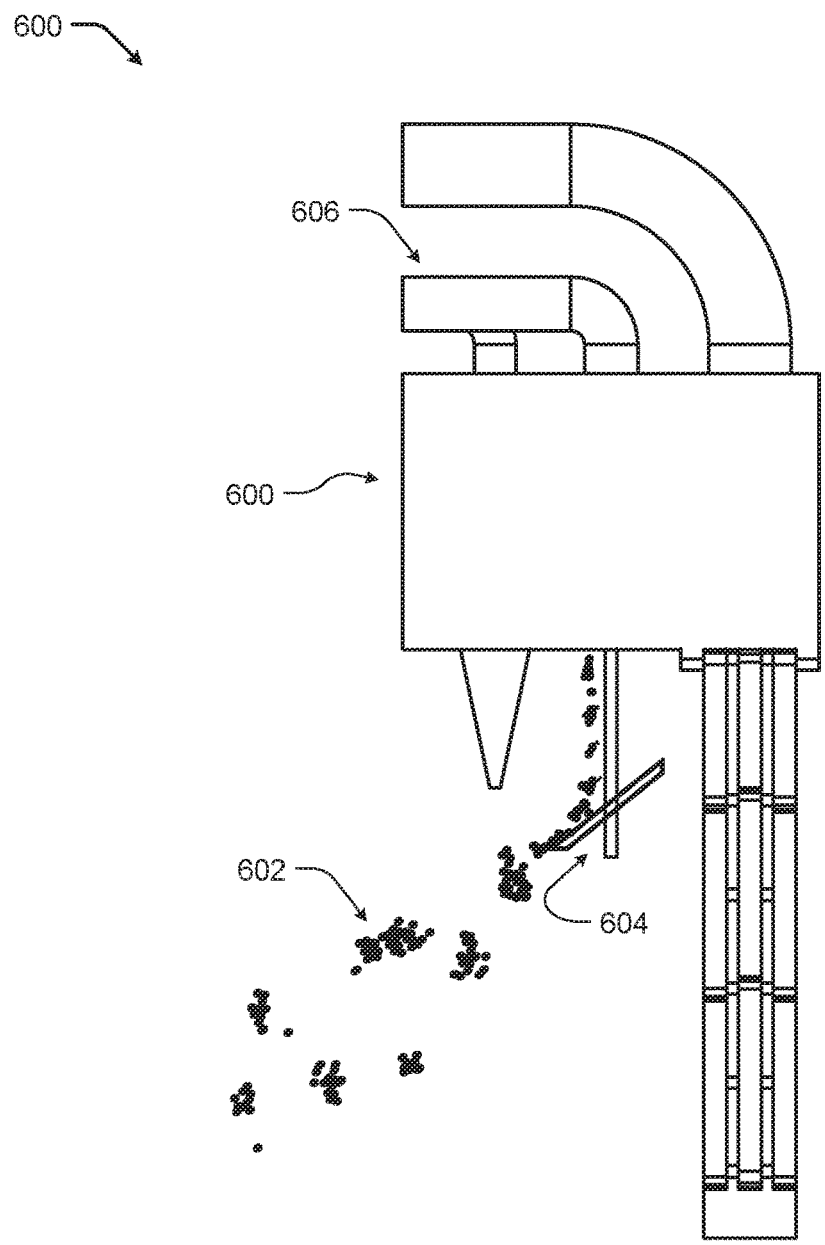
FIG. 6 illustrates another example harvesting platform during feed distribution according to some implementations.
Figure 6:
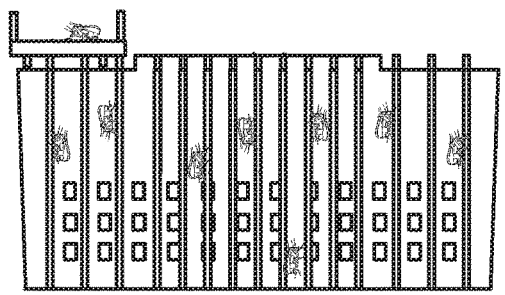

FIG. 6 illustrates another example harvesting platform 600 during feed 602 distribution according to some implementations. In the current example, the harvesting platform 600 is equipped with a feed distribution device 604, shown as a flat angled member. In some cases, feed 602 is dropped onto the angled member of the feed distribution device 604 from a feed tube 606. As the feed 602 hits the flat angled member, the feed 602 is distributed into the room. In the current example, the feed 602 is intended to be distributed evenly or substantially even along the floor of the room. For example, the feed 602 may be dropped from the feed tube 606 onto the angled member as the harvesting platform 600 moves throughout the room. In some instances, the angled member may be equipped with pipes, grooves, bumps, divots, or other types of deflecting apparatus, to cause feed 602 to more evenly or widely distribute.

In some cases, the feed distribution device 604 may be cone shaped, substantially flat, include one or more indentations or bumps, etc. In one example, the feed distribution device 604 may be configured to control the speed or rate of fall of the feed 602 to prevent the feed 602 from injuring the insect population.

Figure 7:
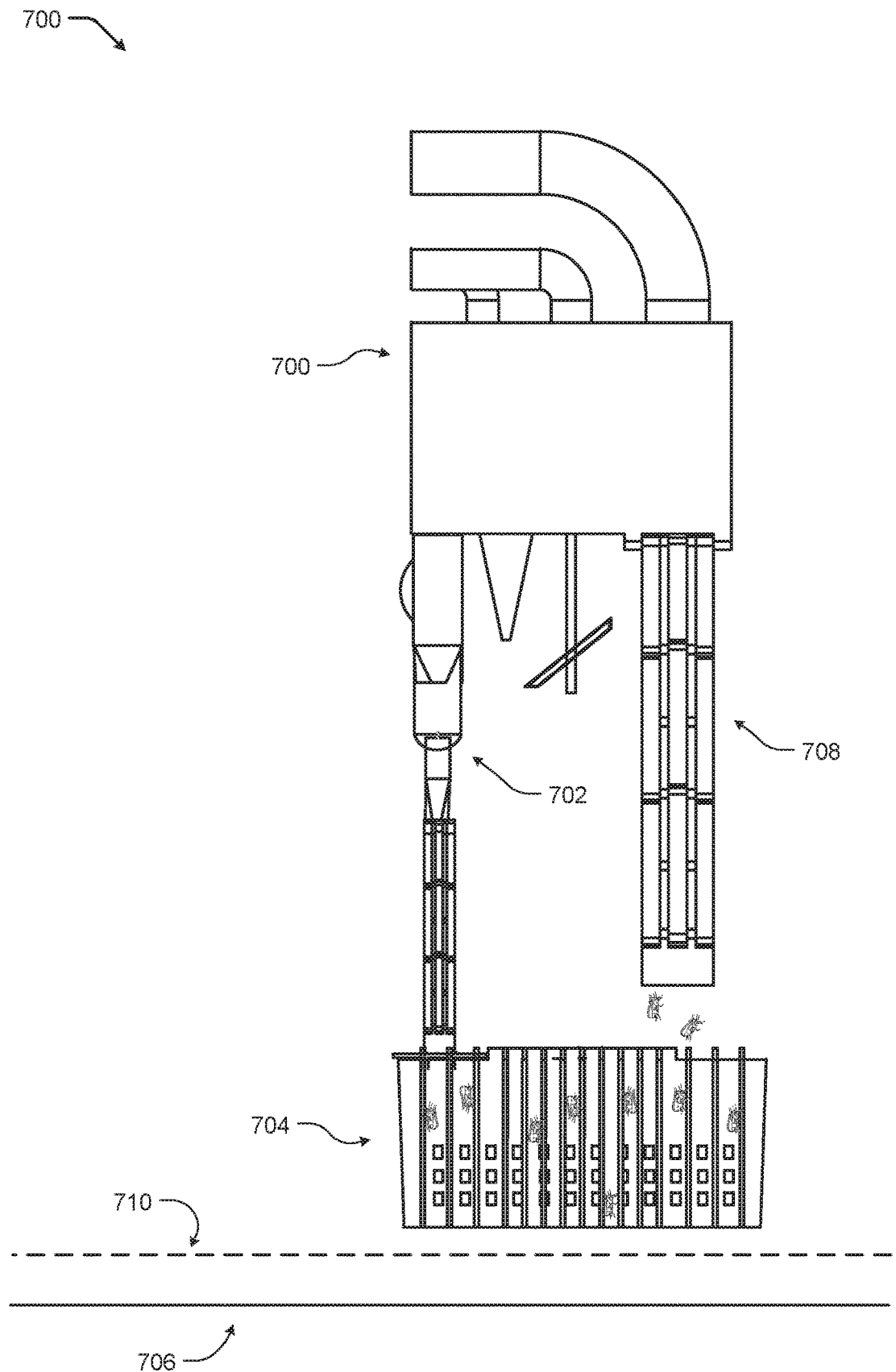
FIG. 7 illustrates another example harvesting platform according to some implementations.

FIG. 7 illustrates another example harvesting platform 700 according to some implementations. In the illustrated example, the harvesting platform 700 includes a lift arm 702. For instance, the lift arm 702 may be configured to raise a habitat, such as habitat 704, from the floor 706 of a room equipped with the harvesting platform 700. As discussed above, the harvesting device 708 may be configured to remove insects above a threshold level off the floor 706 or a threshold distance from the harvesting device 708, generally indicated by line 710. Thus, in this example, the lift arm 702 may move the habitat 704 above the line 710 such that the harvesting device 708 may remove insects located near the bottom of the habitat 704 and thereby reduce the number of insects left in the room after harvesting is complete. In one particular implementation, the agitation device (not shown) may be activated to cause the insects to migrate onto the habitat 704 prior to the lift arm 702 raising the habitat 704 above the threshold 706.

Figure 8:
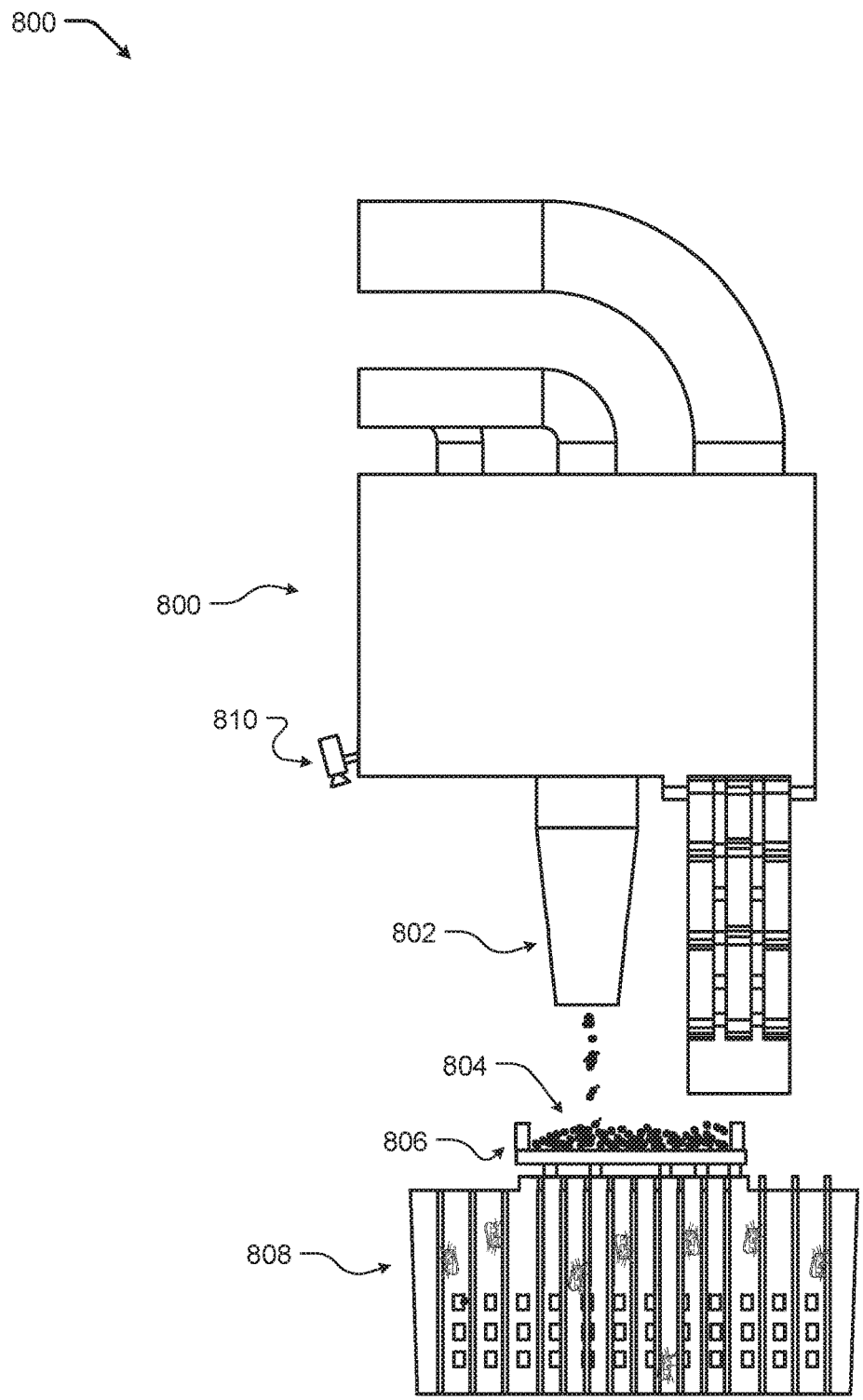
FIG. 8 illustrates another example harvesting platform for use in the system according to some implementations.

FIG. 8 illustrates another example harvesting platform 800 for use in the system according to some implementations. In the current example, the harvesting platform 800 is equipped with a feed distribution device 802. In some cases, feed 804 is delivered to a particular location, such as a feed tray 806 within the room. In these cases, the harvesting platform 800 may first align with the habitat 808 by analyzing data collected by various sensors and image components 810. Unlike the feed distribution, discussed above with respect to FIG. 6, the feed distribution device 802 is configured to dispense feed 804 directly into the feed trays 806 rather than distributing along the floor of the room. For example, by requiring the insects to climb the habitat 808 to feed, the insects may be more easily harvested by the harvesting platform 800. Thus, in some cases, the harvesting platform 800 may be configured to position the feed distribution device 802 with the tray 806 in lieu of or in addition to aligning with the habitat 808.

Figure 9:
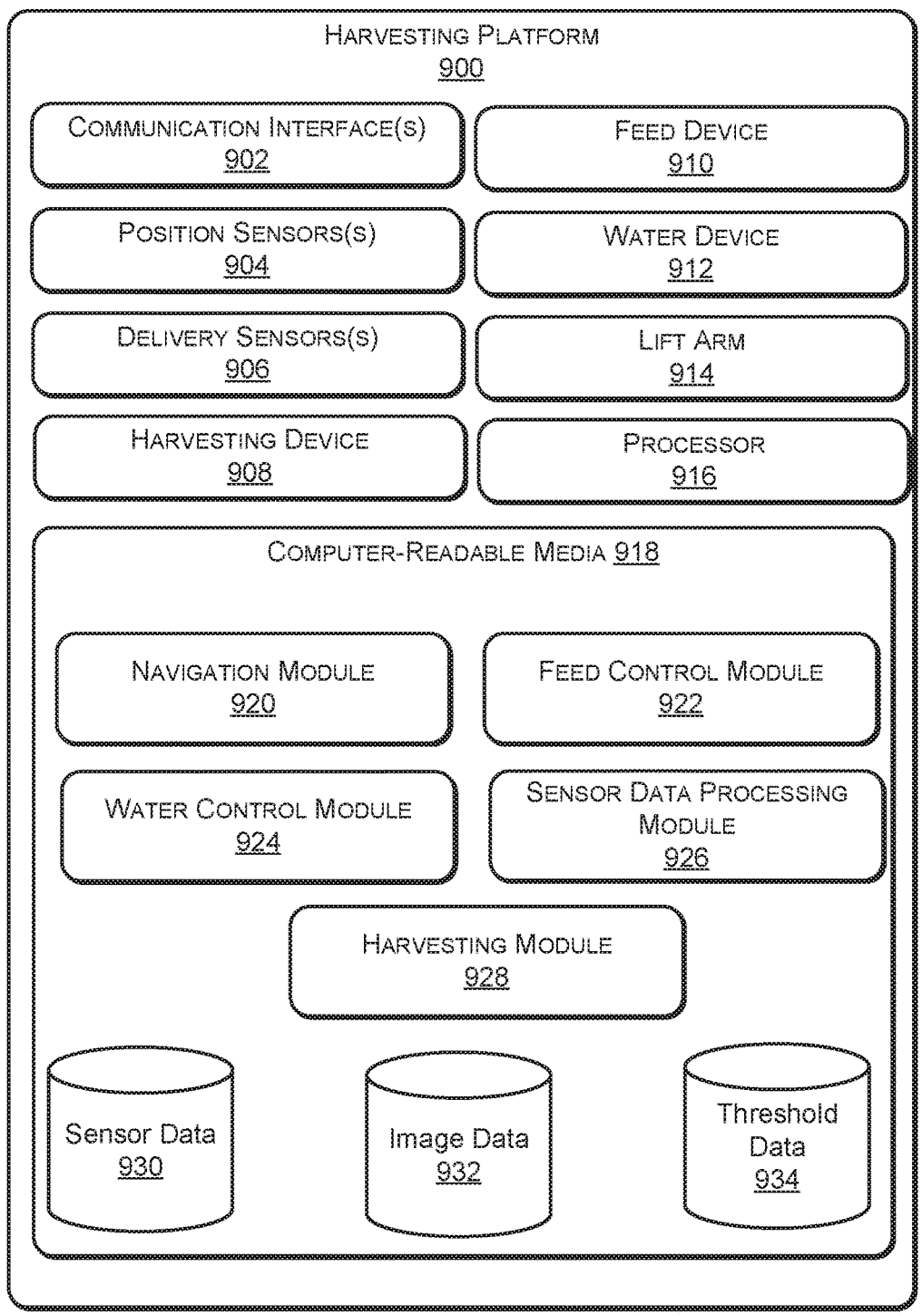
FIG. 9 illustrates example components of a harvesting platform according to some implementations.

FIG. 9 illustrates example components of a harvesting platform 900 according to some implementations. For example, the harvesting platform 900 may be configured or suspended over a room or multiple room used for the cultivation of insects. In some cases, the harvesting platform 900 may be equipped to deliver feed and water to the insects within the room and/or to harvest the insects when the insects achieve a desired life stage or size.

In the illustrated example, the harvesting platform 900 includes one or more communication interfaces 902. The communication interfaces 902 are configured to facilitate communication between one or more networks and/or other devices, such as other harvesting platform, systems equipped on the habitats (e.g., sensors, environmental controls, image components, etc.), and/or devices associated with a management system. For instance, the communication interfaces 902 may provide image and/or sensor data collected during feed deliveries, water deliveries, or harvesting to the management system and/or a facility operator. In some cases, the communication interfaces 902 may also facilitate communication between one or more wireless access points, a master device, and/or one or more other computing devices as part of an ad-hoc or local network systems. The communication interfaces 802 may support both wired and wireless connection to various networks, such as cellular networks, radio, WiFi networks, short-range or near-field networks (e.g., Bluetooth®), infrared signals, local area networks, wide area networks, the Internet, and so forth. In some cases, the communication interfaces 802 may also enable device to device communication such as between harvesting platforms and/or one or more other electronic devices in proximity to the harvesting platform 900.

The harvesting platform 900 may also include various sensors such as position sensors 904 utilized to assist in navigation through a facility and delivery sensors 906 to monitor conditions within a habitat or room. In some cases, the sensors 904 and 906 may include light, optical or photo sensors, mechanical sensors, electrical sensors (magnetic, capacitive, resistive, current, or potential based sensors), weight sensors, thermal or heat sensors, among others. In other cases, the sensors 904 and 906 may include image capturing components, such as cameras and/or video recorders.

The harvesting platform 900 may also include a harvesting device 908, a feed device 910, a water device 912, and/or a lift arm 914, as discussed above. The harvesting device 908 may include a vacuum or suction device, picker arms, or known other harvesting devices. The feed device 910 may be configured to deposit feed at specific locations within a room (e.g., a feed tray) or to distribute the feeds randomly around the room. The water device 912 may also be configured to deliver water into a water tray or other location within the room. The lift arm 914 may be configured to lift or raise habitats within a room off the floor, such that during harvesting, insects may be removed from the entire length or height of the habitat without also collecting waste that develops on the floor of the room over time.

The harvesting platform 900 may also include one or more processors 916, such as at least one or more access components, control logic circuits, central processing units, or processors, as well as one or more computer-readable media 918 to perform the functions associated with the harvesting platform 900. Additionally, each of the processors 916 may itself comprise one or more processors or processing cores.

Depending on the configuration, the computer-readable media 918 may be an example of tangible non-transitory computer storage media and may include volatile and non-volatile memory and/or removable and non-removable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 916.

Several modules such as instructions, data stores, and so forth may be stored within the computer-readable media 918 and configured to execute on the processors 916. For example, as illustrated, the computer-readable media 918 stores a navigation module 920, a feed control module 922, a water control module 924, a sensor data processing module 926, and/or harvesting module 928. The computer-readable media 918 may also be configured to store data, such as sensor data 930 and image data 932 collected by the sensors 904 and 906 and threshold data 934.

The navigation module 912 may be configured to cause the harvesting platform 800 to traverse the space above the room of a facility to deliver feed and water to each designated habitat within the room and/or to preform harvesting sweeps or collections within the room. For example, the navigation module 912 may utilize sensor data 922 and image data 924 to navigate through the facility and/or align for feed distribution, water distribution, and/or harvesting.

The feed control module 914 may utilize the sensor data 922 and image data 924 to position the harvesting platform 900 with respect to the habitat and to dispense a desired amount of feed onto each tray or at a desired rate. For example, the feed control module 914 may cause a different amount or types of feed to be distributed to different rooms or at different times of the day, month, or year. The water control module 916 may also utilize the sensor data 922 and image data 924 to position the harvesting platform 900 with respect to the habitat and to dispense a desired amount of water onto each water tray or at a desired rate. In some cases, the water control module 916 may cause the processors 908 to analyze the sensor data 922 and/or image data 924 to determine if a specific water tray should be refilled.

The sensor data processing module 918 may process the sensor data 922 and image data 924 to assist with monitoring a health of the insects or a state of the cultivating room. For example, sensor data processing module 918 may be configured to analyze the sensor data 922 and image data 924 to determine that population of the room has decreased by more than a threshold or expected amount. In some cases, the sensor data processing module 918 may also monitor an amount of feed, amount of water, environmental conditions of the room associated with the harvesting platform 900. For example, the sensor data processing module 918 may determine that the insects are in need of additional feed, water, or are ready to harvest. In each condition, the sensor data processing module 918 may cause the harvesting module 920 and/or the feed control module 914 to begin operations. In some cases, the sensor data processing module 918 may be configured to cause the communication interfaces 902 to provide the sensor data 930 and/or image data 932 to a management system or facility operator for further processing or review. For example, the sensor data processing module 926 may determine that the sensor data 930 and/or the image data 932 indicates an issue or concern with respect to the insect population and to cause an alert or notification to be provided to the management system or other devices associated with an operator.

The harvesting module 920 may be configured to cause the harvesting platform 900 to monitor the sensor data 932 and the room to determine if the harvesting platform 900 should initiate a sweep or harvest of the room. In some cases, the harvesting module 928 may be configured to determine the amount of suction associated with the harvesting device 908 and/or if the lift arm 914 should raise or lower habitats within the room. In one specific example, the harvesting module 928 may be configured to activate the agitation device within the room to cause the insects to migrate up the habitats prior to harvesting.

Figure 10:
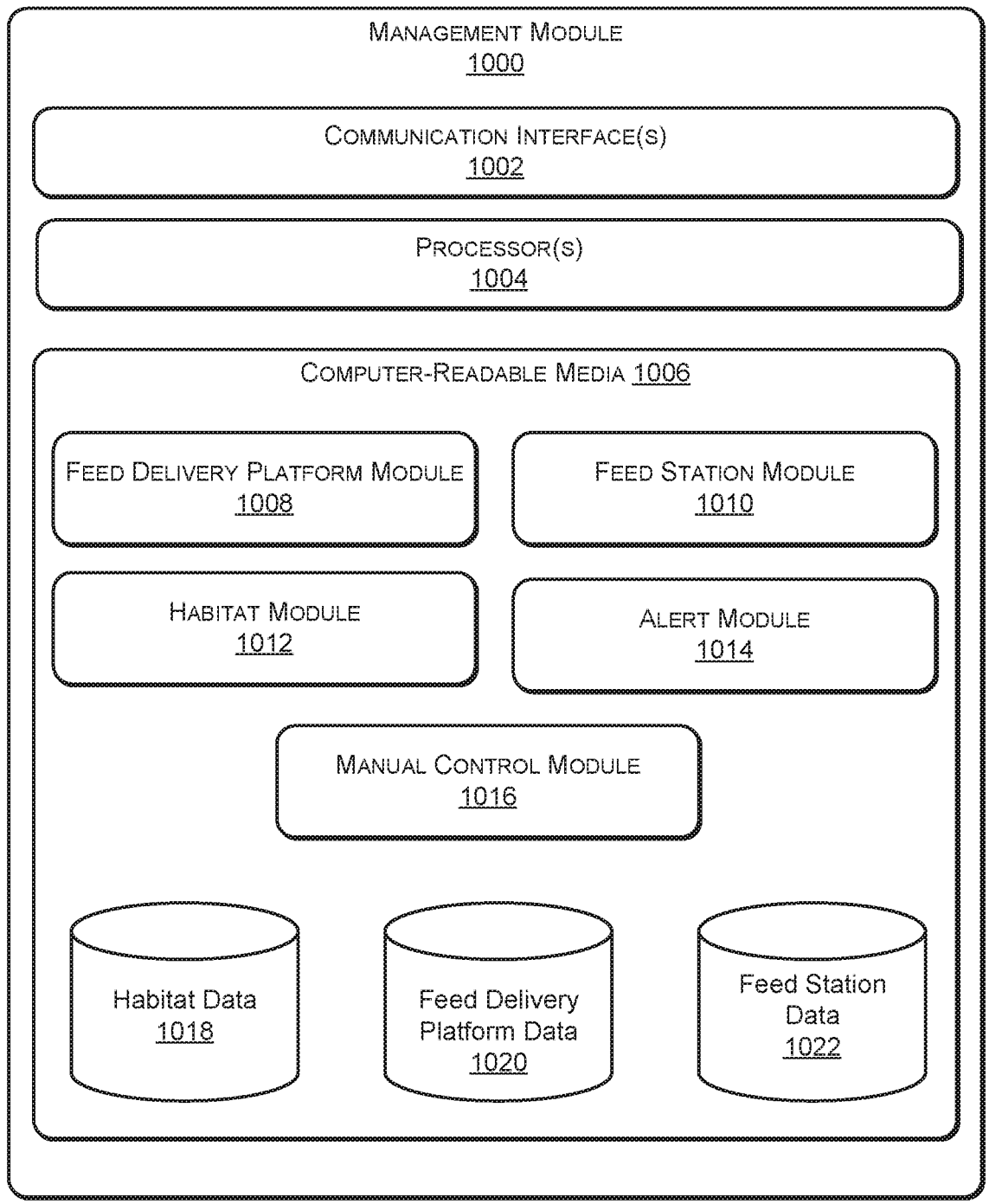
FIG. 10. Illustrates example components of a management system associated with one or more harvesting platforms according to some implementations.

FIG. 10 illustrates example components of a management system 1000 associated with one or more harvesting platforms according to some implementations. For example, the management system 1000 may be configured to process image and/or sensor data collected within a facility from the harvesting platforms, habitats, rooms, etc. The management system 1000 may then control and/or coordinate the operation of the harvesting platforms.

In the illustrated example, the management system 1000 includes one or more communication interfaces 1002. The communication interfaces 1002 are configured to facilitate communication between one or more networks and/or other devices, such as harvesting platforms, habitats, and/or other devices associated with the facility/operators. For instance, the communication interfaces 1002 may provide image and/or sensor data collected during feed deliveries to devices associated with facility operators. In some cases, the communication interfaces 1002 may also facilitate communication between one or more wireless access points, a master device, and/or one or more other computing devices as part of an ad-hoc or local network systems. The communication interfaces 1002 may support both wired and wireless connection to various networks, such as cellular networks, radio, WiFi networks, short-range or near-field networks (e.g., Bluetooth®), infrared signals, local area networks, wide area networks, the Internet, and so forth.

The management system 1000 may also include one or more processors 1004, such as at least one or more access components, control logic circuits, central processing units, or processors, as well as one or more computer-readable media 1006 to perform the functions associated with the management system 1000. Additionally, each of the processors 1004 may itself comprise one or more processors or processing cores.

Depending on the configuration, the computer-readable media 1006 may be an example of tangible non-transitory computer storage media and may include volatile and non-volatile memory and/or removable and nonremovable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 1004.

Several modules such as instructions, data stores, and so forth may be stored within the computer-readable media 1006 and configured to execute on the processors 1004. For example, as illustrated, the computer-readable media 1006 stores a feed delivery module 1008, a water delivery module 1010, a harvesting module 1012, a monitoring module 1014, and a manual control module 1016. The computer-readable media 1006 may also be configured to store data, such as habitat data 1018 collected and received by the habitats within the room, room data 2020 collected and received from sensors and image components within the room, and harvester data 2022 collected and received from the harvester systems within the facility.

The feed delivery module 1008 may be configured to dispatch and monitor feed delivery by the harvesting platform. In some cases, the feed delivery module 2008 may be configured to provide navigation paths to the harvesting platform, locations or positions at which feed should be delivered too, and/or initiation signals to start feed delivery by the harvesting platforms.

The water delivery module 1010 may be configured to dispatch and monitor water delivery by the harvesting platform. In some cases, the water delivery module 1010 may be configured to provide navigation paths to the harvesting platform, locations or positions at which water should be delivered too, and/or initiation signals to start water delivery by the harvesting platforms. In some cases, the feed delivery module 1008 and the water delivery module 1010 may be combined.

The harvesting module 1012 may be configured to determine if the insect population should be harvested. For example, the harvesting module 1012 may analyze the habitat data 1018, room data 1020, and/or the harvester data 1022 to determine when/if an insect population has reached maturity or if an issue as occurred to cause a premature harvesting of the insects.

Figure 11:
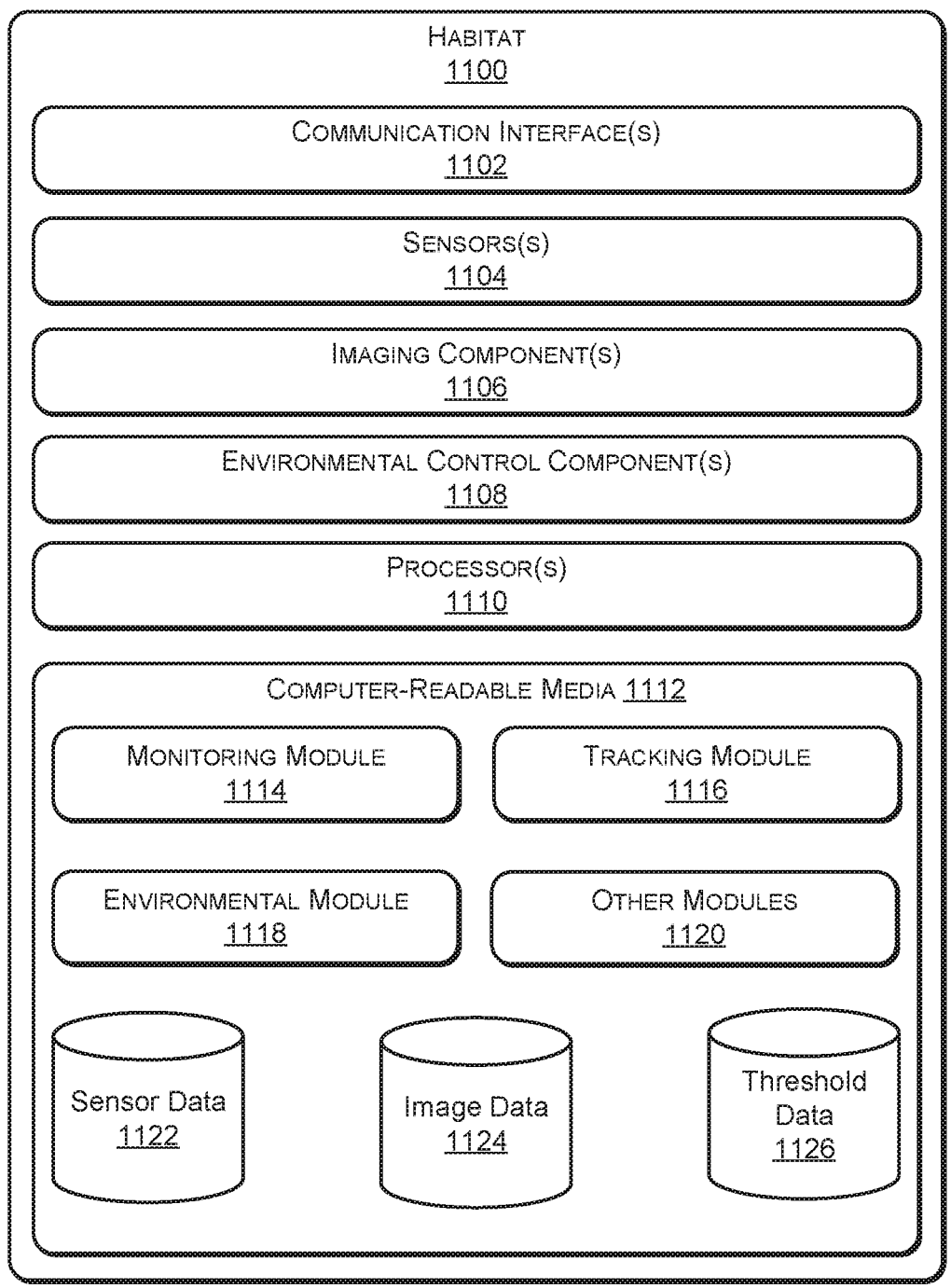
FIG. 11 illustrates example components of a habitat configured to receive feed/water from a harvesting platform according to some implementations.

The manual control module 1016 may allow a system or facility operator to control the harvester system to provide manual feed delivery, manual water delivery, manual harvesting and/or to insect the insect population within the room. For instance, since the room is sealed to human contract to prevent inadvertently damaging the population, the operator may utilize a camera installed on the harvesting platform to inspect the progress or life cycle stage of the insects within the room. FIG. 11 illustrates example components of a habitat 1100 configured to receive feed/water from a harvesting platform according to some implementations. In the illustrated example, the habitat 1100 may be a vertical unit within a room for cultivating insects. The habitat 1100 may be placed in the room to assist with harvesting of insects and to increase the overall surface space within the room and, thereby, to incases the population that maybe raised within the room. In some cases, the habitat 1100 may be configured to monitor the insects within the habitat 1100 to determine, for example, when the insects should be harvested and/or to provide information and data usable by the harvesting platform.

In the illustrated example, the habitat 1100 includes one or more communication interfaces 1102. The communication interfaces 1102 are configured to facilitate communication between one or more networks and/or other devices of the harvesting platform and/or a management system. For instance, the communication interfaces 1102 may provide a notification to the harvesting platform or the management system when food levels within the room are below a threshold amount. In some cases, the communication interfaces 1102 may also facilitate communication between one or more wireless access points, a master device, and/or one or more other computing devices as part of an ad-hoc or local network system. The communication interfaces 1102 may support both wired and wireless connection to various networks, such as cellular networks, radio, WiFi networks, short-range or near-field networks (e.g., Bluetooth®), infrared signals, local area networks, wide area networks, the Internet, and so forth. In some cases, the communication interfaces 1102 may also enable device to device communication such as between habitats 1100 within a room.

The habitat 1100 may also include various sensors 1104 that may collect data that is usable to determine a population, health, insect size, food levels, water levels, etc. within the habitat 1100. For example, the habitat 1100 may include optical, or photo sensors, mechanical sensors (e.g., pressure, force, or motion sensors), electrical sensors (capacitive, resistive, current, or potential based sensors), weight sensors, thermal or heat sensors, among others.

In some cases, a plurality of imaging components 1106 may be used to monitor the insects within the habitat 1100. For example, the habitat 1100 may include a three-dimensional camera system, an infrared camera, and/or a red-green-blue camera. In one example, the three-dimensional and infrared camera may be configured to capture information related to depths, location, and movement of objects within the field of view. The red-green-blue camera may be configured to detect edges of objects by identifying changes in color within the field of view. In some cases, the habitat 1100 may also include additional imaging components for tracking the movement of insects within the habitat 1100. For example, the habitat 1100 may include one or more motion sensors or thermal sensors.

The habitat 1100 may also include one or more environmental control components 1108. The environmental control components 1108 may be utilized to control environmental factors, such as wind, temperatures, humidity, salinity, etc. within the habitat 1100 to encourage proper growth based on life stages and desired crop output.

The habitat 1100 includes one or more processors 1110, such as at least one or more access components, control logic circuits, central processing units, or processors, as well as one or more computer-readable media 1112 to perform the functions associated with the habitat 1100. Additionally, each of the processors 1110 may itself comprise one or more processors or processing cores.

Depending on the configuration, the computer-readable media 1112 may be an example of tangible non-transitory computer storage media and may include volatile and nonvolatile memory and/or removable and nonremovable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 1110.

Several modules such as instructions, data stores, and so forth may be stored within the computer-readable media 1112 and configured to execute on the processors 1110. For example, as illustrated, the computer-readable media 1112 stores a monitoring module 1114, a tracking module 1116, an environmental module 1118, as well as other modules 1120. The computer-readable media 1112 may also be configured to store data, such as sensor data 1122 collected by the sensors 1104, image data 1124 captured by the imaging components 1106, and threshold data 1126 such as various desired egg densities or range of densities.

The monitoring module 1114 may be configured to analyze the sensor data 1122 and the image data 1124 and to determine insect size, health, age, movement, activity level, etc. For example, the monitoring module 1114 may be configured to determine when the insects have reached an appropriate size for harvesting and to cause the communication interfaces 1102 to alert another system such as a robotic arm that the threshold has been met to further cause the robotic arm to collect and move the insects to a waste removal and/or processing area.

The tracking module 1116 may be configured to track the movement of insects within the habitat 1100 and/or room based on the sensor data 1122 and the image data 1124, and to again cause the communication interfaces 1102 to alert another system such as the harvesting platform when the tracking module 1116 determines that a threshold insect size has been reached.

The environmental module 1118 may be configured to analyze the data provided by the monitoring module 1114 and the tracking module 1116 and to determine an environmental adjustment based on the data. For example, the environmental module 1118 may determine if the environmental conditions become less than optimal for raising insects.

Figure 12:
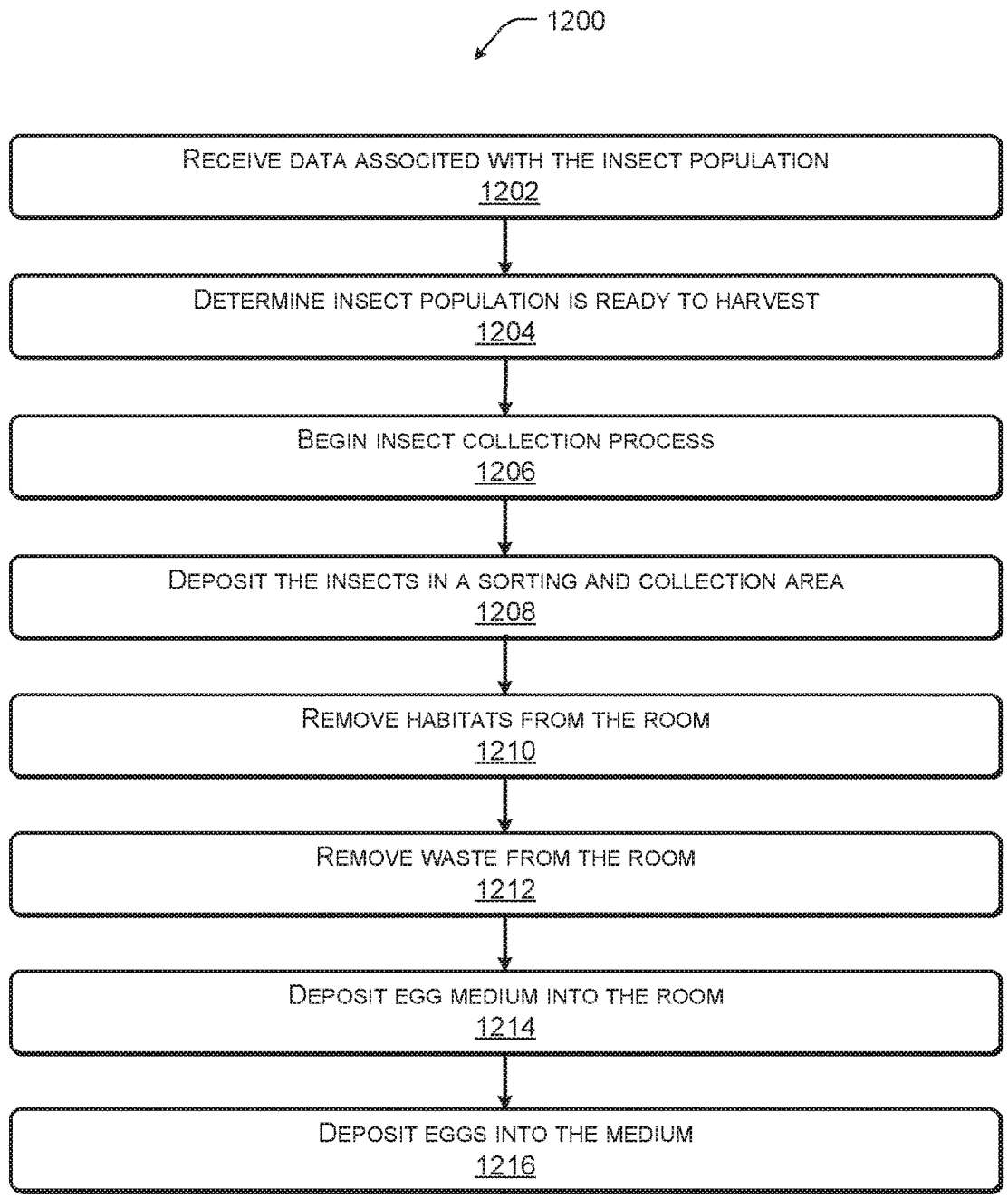
FIG. 12 illustrates an example flow diagram showing an illustrative process associated with the harvesting of an insect population according to some implementations.
Figure 13:
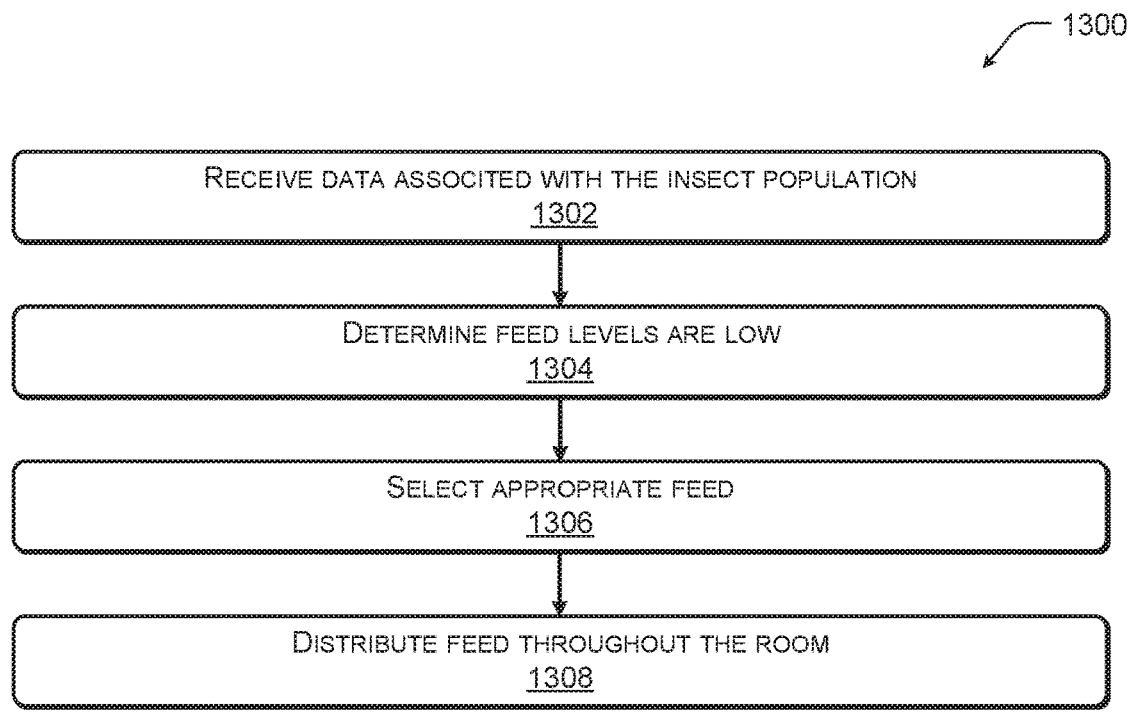
FIG. 13 illustrates an example flow diagram showing an illustrative process associated with the delivering of feed to an insect population according to some implementations.
Figure 14:
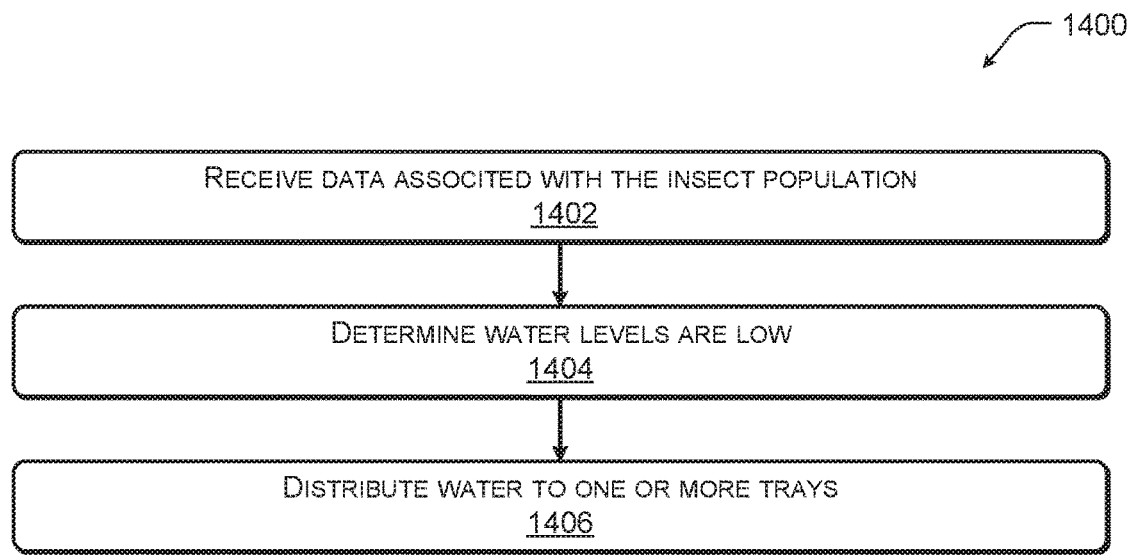
FIG. 14 illustrates an example flow diagram showing an illustrative process associated with the delivering of water to an insect population according to some implementations.

FIGS. 12-14 provide example flow diagrams illustrating example processes for implementing the feed delivery systems described above. The processes are illustrated as a collection of blocks in a logical flow diagram, which represent a sequence of operations, some or all of which can be implemented in hardware, software or a combination thereof. In the context of software, the blocks represent computer-executable instructions stored on one or more computer-readable media that, which when executed by one or more processors, perform the recited operations. Generally, computer-executable instructions include routines, programs, objects, components, data structures and the like that perform particular functions or implement particular abstract data types.

The order in which the operations are described should not be construed as a limitation. Any number of the described blocks can be combined in any order and/or in parallel to implement the process, or alternative processes, and not all of the blocks need be executed. For discussion purposes, the processes herein are described with reference to the frameworks, architectures and environments described in the examples herein, although the processes may be implemented in a wide variety of other frameworks, architectures or environments.

FIG. 12 illustrates an example flow diagram showing an illustrative process 1200 associated with the harvesting an insect population according to some implementations. As discussed above, the insects may live their entire life within a room sealed from outside pathogens and/or containments. A harvesting platform may be configured within the room to provide feed, water, and to harvest the insect population. In some cases, the harvesting platform may be associated with multiple rooms such that one harvesting device may supply feed, water, and harvest populations within multiple rooms.

At 1202, the harvesting platform and/or management system may receive data, such as sensor data, image data, or other data, associated with the insect population within the room. In some cases, the data may be collected by sensors within the room, on the habitats, associated with the harvesting platform, etc.

At 1204, the harvesting platform and/or management system may determine that the insect population is ready to harvest. For example, the data may indicated the insects have on average reached a desire size, maturity, etc. For instance, the data may be analyzed to determine health, color, size, activity, etc. associated with the population in order to determine the population is ready to harvest.

At 1206, the harvesting platform may begin a sweep of the room. For example, the harvesting platform may lower a vacuum collection system to a position proximate to the insect population (e.g., near the top of the habitats or near the floor when habitats are not in use). In some cases, the harvesting platform may be configured to raise or elevate each habitat prior to collecting the insect population associated therewith.

At 1208, the harvesting platform may deposit the insects in a sorting and harvesting area. For example, the insects may be piped or provided directly from the vacuum to a sorting and harvesting area where the different parts of the insects may be separated according to use (e.g., the harvesting platform is in fluid communication with the sorting and harvesting area). In other cases, the harvesting platform may move to the sorting and harvesting area and unload the collected insects.

At 1210, the harvesting platform may remove the habitats from the room. For example, the harvesting platforms may grab and raise each habitat and transport the habitat to a cleaning facility. In other case, the facility operator may enter the room following harvesting and remove the habitats.

At 1212, the harvesting platform may remove the waste from the room. For example, using either the vacuum for harvesting or a second vacuum. In either case, the vacuum may be in fluid communication with a waste repository rather than the sorting and harvesting area, as was the case at 1208.

At 1214, the harvesting platform may deposit an egg medium into the floor of the room to grow another population of insects. For example, the harvesting platform may use the vacuum in reverse, the feed distribution device, or another device to fill the floor of the room with sand or other material.

At 1216, the harvesting platform may deposit eggs into the medium. For example, the eggs may be buried into the medium or place atop the medium depending on the type of insect being cultivated.

FIG. 13 illustrates an example flow diagram showing an illustrative process 1300 associated with the delivering feed to an insect population according to some implementations. As discussed above, the insects may live their entire life within a room sealed from outside pathogens and/or containments. A harvesting platform may be configured within the room to provide feed, water, and to harvest the insect population. In some cases, the harvesting platform may be associated with multiple rooms such that one harvesting device may supply feed, water, and harvest populations within multiple rooms.

At 1302, the harvesting platform and/or management system may receive data, such as sensor data, image data, or other data, associated with the insect population within the room. In some cases, the data may be collected by sensors within the room, on the habitats, associated with the harvesting platform, etc.

At 1304, the harvesting platform and/or management system may determine the feed levels are low based on the data received. For example, the data may be analyzed to determine an amount of feed remaining in the room. In other cases, the harvesting platform may deliver feed on schedule and the data may be utilized to determine if the insects are consuming desired levels of feed.

At 1306, the harvesting platform and/or the management system may select an appropriate feed. For example, the data may be analyzed to determine a mature of life cycle associated with the insects and a feed having a nutritional balance based on the maturity level may be selected.

At 1308, the harvesting platform may distribute the feed throughout the room. For example, as discussed above, the harvesting platform may include a distribution device to cause the feed to spread out over the room as the feed is delivered from the harvesting platform.

FIG. 14 illustrates an example flow diagram showing an illustrative process 1400 associated with the delivering water to an insect population according to some implementations. As discussed above, the insects may live their entire life within a room sealed from outside pathogens and/or containments. A harvesting platform may be configured within the room to provide feed, water, and to harvest the insect population. In some cases, the harvesting platform may be associated with multiple rooms such that one harvesting device may supply feed, water, and harvest populations within multiple rooms.

At 1402, the harvesting platform and/or management system may receive data, such as sensor data, image data, or other data, associated with the insect population within the room. In some cases, the data may be collected by sensors within the room, on the habitats, associated with the harvesting platform, etc.

At 1404, the harvesting platform and/or management system may determine the water levels are low based on the data received. For example, the data may be analyzed to determine an amount of water remaining various trays. In other cases, the harvesting platform may deliver water on schedule and the data may be utilized to determine the amount of water to deliver to each tray.

At 1406, the harvesting platform may distribute the water to one or more trays. For example, as discussed above, the harvesting platform may include a water distribution device to cause the water to fill various trays within the room Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A harvesting platform comprising:
   at least one support for suspending the harvesting platform over a room, the support movable with respect to the room in a first direction and the harvesting platform movable with respect to the at least one support in a second direction, the second direction perpendicular to the first direction;
   a first feed delivery device;
   a water delivery device;
   a first feed tube to deliver a first type of feed from a first feed source to the feed delivery device wherein the first feed delivery device includes an angled member positioned below the first feed tube, the angled member to be impacted by feed exiting the feed tube such that the feed is disturbed in a substantially even patter;
   a water tube to deliver water from a water source to the water delivery device;
   a sensor to collect data associated with an environment associated with an insect cultivating room;
   a harvesting device to apply a predetermined level of suction to remove insects from the insect cultivating room;
   one or more processors; and
   computer-readable storage media storing computer-executable instructions, which when executed by the one or more processors cause the one or more processors to:
   receive the data from the sensor;
   cause the harvesting platform to orient and couple with a habitat located within the room; and
   cause the harvesting device to apply a vacuum force over the habitat.

2. The harvesting platform as recited in claim 1, further comprising a second feed tube to deliver a second type of feed from a second feed source to the feed delivery device.

3. The harvesting platform as recited in claim 1, further comprising a harvesting device configured to be lowered into the room.

4. The harvesting platform as recited in claim 3, further comprising an extendable lift arm configured to couple to a habitat.

5. The harvesting platform as recited in claim 1, wherein the predetermined level of suction causes insects at a height above six inches off of a floor of the room to be harvested.

6. A harvesting platform comprising:
   at least one support for suspending the harvesting platform over a room and allowing the harvesting platform to move over the room;
   a sensor to collect data associated with an environment associated with an insect cultivating room;
   a harvesting device to apply a predetermined level of suction to remove insects from the insect cultivating room;
   an extendable lift arm;

one or more processors; and computer-readable storage media storing computer-executable instructions, which when executed by the one or more processors cause the one or more processors to:
- receive the data from the sensor;
- cause the harvesting platform to orient with a habitat located within the room;
- cause the extendable lift arm to couple to the habitat; and
- cause the harvesting device to apply a vacuum force over the habitat.

7. The harvesting platform as recited in claim 6, wherein the harvesting device is extendable to remove at least some of the insects from walls of the habitat but not along a floor of the insect cultivating room.

8. The harvesting platform as recited in claim 6, further comprising:
- a first feed delivery device;
- a first feed tube to deliver a first type of feed from a first feed source to the feed delivery device; and
- a second feed tube to deliver a second type of feed from a second feed source to the feed delivery device.

9. The harvesting platform as recited in claim 6, further comprising:
- a water delivery device; and
- a water tube to deliver water from a water source to the water delivery device.

10. The harvesting platform as recited in claim 6, wherein the at least one support for suspending the harvesting platform over the room and allowing the harvesting platform to move over the room includes:
- a first beam having a first end and a second end opposite the first end, and wherein the harvesting platform is coupled to the first beam between the first end and the second end to allow the harvesting platform to move in a first direction and in a second direction, the second direction opposite the first direction;
- a second beam coupled to the first beam at the first end; and
- a third beam coupled to the first beam at the second end, and wherein the first beam moves in a third direction and a fourth direction along the second beam and the third beam, the third direction perpendicular to the first direction and the second direction and the fourth direction opposite the third direction.

11. The harvesting platform as recited in claim 10, further comprising:
- a communication interface to establish a communication channel with a management system; and
- wherein the computer-readable storage media stores additional computer-executable instructions, which when executed by the one or more processors cause the one or more processors to cause the communication interface to send the sensor data to the management system.

12. The harvesting platform as recited in claim 6, wherein the computer-readable storage media stores additional computer-executable instructions, which when executed by the one or more processors cause the one or more processors to determine, based at least in part on the sensor data, at least one of the following:
- a size of an insect population;
- a health of the insect population;
- an amount of feed to deliver;
- an amount of water to deliver; or
- a developmental state of the insect population.

13. The harvesting platform as recited in claim 6, wherein the computer-readable storage media stores additional computer-executable instructions, which when executed by the one or more processors cause the one or more processors to cause the communication interface to:
- determine a predetermined period of time has elapsed; and
- in response to the predetermined period of time elapsing, cause the harvesting platform to re-orient with the habitat and re-causing the harvesting device to apply a second vacuum force.

14. The harvesting platform as recited in claim 13, wherein the second vacuum force is substantially equal to the first vacuum force.

15. The harvesting platform as recited in claim 13, wherein the second vacuum force differs from the first vacuum force.

16. A harvesting platform comprising:
- at least one support for suspending the harvesting platform over an insect cultivating room;
- a sensor to collect data associated with an environment associated with an insect cultivating room;
- at least one component to determine a size of an insect population based at least in part on the sensor data; and
- a harvesting device to apply a predetermined level of suction to remove insects from the insect cultivating room;
- an extendable lift arm;
- one or more processors; and
- computer-readable storage media storing computer-executable instructions, which when executed by the one or more processors cause the one or more processors to:
  - cause the harvesting platform to orient with a habitat located within the room based at least in part on the sensor data;
  - cause the extendable lift arm to couple to the habitat; and
  - cause the harvesting device to apply a vacuum force over the habitat.

17. The harvesting platform as recited in claim 16, further comprising:
- a first feed delivery device;
- a first feed tube to deliver a first type of feed from a first feed source to the feed delivery device; and
- a second feed tube to deliver a second type of feed from a second feed source to the feed delivery device.

18. The harvesting platform as recited in claim 16, further comprising:
- a water delivery device; and
- a water tube to deliver water from a water source to the water delivery device.

19. The harvesting platform as recited in claim 16, wherein the predetermined level of suction removes insects within the top seventy-five percent of a habitat located within the room.

20. The harvesting platform as recited in claim 16, further comprising a sensor to collect data associated with the room.

* * * * *